United States Patent [19]

Kurn et al.

[11] Patent Number: 4,868,104

[45] Date of Patent: Sep. 19, 1989

[54] HOMOGENEOUS ASSAY FOR SPECIFIC POLYNUCLEOTIDES

[75] Inventors: Nurith Kurn, Palo Alto; Chander Bahl, San Mateo; Edwin F. Ullman, Atherton, all of Calif.

[73] Assignee: Syntex (U.S.A.) Inc., Palo Alto, Calif.

[21] Appl. No.: 773,386

[22] Filed: Sep. 6, 1985

[51] Int. Cl.$^4$ .............. G01N 33/566; G01N 33/537; C12Q 1/68; C12Q 1/70

[52] U.S. Cl. .......................................... 435/6; 435/5; 435/810; 436/501; 436/537; 436/538; 436/808; 935/2; 935/3; 935/78

[58] Field of Search .............. 435/5, 6, 810; 436/501, 436/537, 538, 808; 935/2, 3, 78

[56] References Cited

U.S. PATENT DOCUMENTS

| | | | |
|---|---|---|---|
| 4,193,983 | 3/1980 | Ullman et al. | 436/537 X |
| 4,313,734 | 2/1982 | Leuvering | 436/808 X |
| 4,522,922 | 6/1985 | Carro et al. | 436/501 X |
| 4,563,417 | 1/1986 | Albarella et al. | 436/504 X |
| 4,563,419 | 1/1986 | Ranki et al. | 436/808 X |
| 4,623,627 | 11/1986 | Huang et al. | 436/548 X |
| 4,749,647 | 6/1988 | Thomas et al. | 435/7 X |
| 4,751,177 | 6/1988 | Stabinsky | 435/6 |

FOREIGN PATENT DOCUMENTS

| | | |
|---|---|---|
| 0070685 | 1/1983 | European Pat. Off. . |
| 0079139 | 5/1983 | European Pat. Off. . |
| 0130515 | 1/1985 | European Pat. Off. . |
| 0139489 | 5/1985 | European Pat. Off. . |
| 0153873 | 9/1985 | European Pat. Off. . |
| 0154505 | 9/1985 | European Pat. Off. . |
| WO8603227 | 6/1986 | World Int. Prop. O. . |
| WO8502628 | 6/2085 | World Int. Prop. O. . |

Primary Examiner—Esther M. Kepplinger
Assistant Examiner—Richard Wagner
Attorney, Agent, or Firm—Theodore J. Leitereg

[57] ABSTRACT

A method for determining the presence of a polynucleotide analyte in a sample suspected of containing the analyte is disclosed. The method comprises combining in an assay medium the sample and first and second polynucleotide reagents complementary to the analyte. Each of the first and second reagents hybridize with a different region of the analyte. The first reagent contains means for rendering the first reagent non-covalently polymerizable. The second reagent contains means for rendering the second reagent detectable. The sample and the first and second reagents are combined in the assay medium under conditions for polymerizing the first reagent wherein the second reagent becomes bound to the polymerized first reagent only when the analyte is present in the sample. A determination is then made as to whether the second reagent has become bound to the polymerized first reagent. The method has broad application for determining the presence of a polynucleotide analyte such as DNA, RNA, the genomes of viruses, bacteria, molds, fungi, and fragments thereof, and the like. Preferred means for rendering the first reagent non-covalently polymerizable includes a repeating oligonucleotide sequence covalently bound to the first reagent.

96 Claims, No Drawings

HOMOGENEOUS ASSAY FOR SPECIFIC POLYNUCLEOTIDES

BACKGROUND OF THE INVENTION

1. Field of the Invention

Nucleic acid hybridization has been employed for investigating the identity of nucleic acids. Hybridization is based on complementary base pairing. When single stranded nucleic acids are incubated in solution, complementary base sequences pair to form double stranded stable hybrid molecules. The ability of single stranded deoxyribonucleic acid (DNA) or ribonucleic acid (RNA) to form a hydrogen bonded structure with its complementary nucleic acid sequence has been employed as an analytical tool in recombinant DNA research. The availability of radioactive nucleotide triphosphates of high specific activity and the synthetic methods of incorporating these nucleotides into nucleic acid probes has made it possible to identify, isolate, and characterize various nucleic acid sequences of biological interest. Nucleic acid hybridization has great potential in diagnosing disease states mediated by alteration in nucleic acid composition of the host. These alterations in nucleic acid composition will include genetic or environmental change in DNA by insertions, deletions, point mutations, or acquiring foreign DNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine has not occurred because of the unavailability of a simple, sensitive, automated, nonisotopic, rapid method of DNA hybridization analysis.

Current methods for detecting DNA probes generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at elevated temperatures to remove unbound probe. The support is then dried and the hybridized material is detected by autoradiography or by colorimetric methods.

The current methods are slow and labor intensive. For that reason application of the current methods in clinical laboratories has not occurred. For such an application a simple, rapid, nonisotopic, homogeneous method for detecting DNA sequences is necessary.

2. Description of the Prior Art

Langer, et al., *Proc. Natl. Acad. Sci. USA*, (1981) 78, 6633–6637 discloses the enzymatic synthesis of biotin labelled polynucleotides and the use of these materials as novel nucleic acid affinity probes. The detection of viral genomes in cultured cells and paraffin imbedded tissue sections using biotin labelled hybridization probes is discussed by Brigati, et al., *Virology*, (1983) 126, 32–50. U.S. Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European patent application No. 83106112.2 (Priority U.S. patent application No. 391,440 filed June 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153.

SUMMARY OF THE INVENTION

The invention disclosed herein includes methods and reagents for determining the presence of a polynucleotide analyte in a sample suspected of containing the analyte. The method comprises combining in an assay medium the sample and first and second polynucleotide reagents complementary to the analyte. The first and second reagents hybridize with a different region of the analyte. The first reagent contains means for rendering the first reagent non-covalently polymerizable. The second reagent contains means for rendering the second reagent detectable. The sample and the first and second polynucleotide reagents are combined in the assay medium under conditions for polymerizing the first reagent wherein the second reagent becomes bound to the polymerized first reagent only when the analyte is present in the sample. Preferred means for rendering the first reagent non-covalently polymerizable is a repeating oligonucleotide sequence covalently bound to the first reagent. The method further includes detecting whether the second reagent has become bound to the polymerized first reagent. The method of the invention has particular application to the determination of the presence of polynucleotide analytes such as DNA, RNA, the genomes of viruses, bacteria, molds, fungi, and fragments thereof, and the like. The invention also includes kits containing in a packaged combination the reagents for carrying out an assay in accordance with the above method.

DESCRIPTION OF THE SPECIFIC EMBODIMENTS

The present assay method generally relates to the detection of a polynucleotide analyte in a sample suspected of containing such analyte where the method involves agglutination. The improvement of the present invention comprises employing complementary oligonucleotide sequences to cause the agglutination in such assay.

Generally, the method of the invention comprises combining in an assay medium the sample and first and second polynucleotide reagents complementary to the analyte. Each of the first and second reagents hybridize with a different region of the analyte. The first reagent contains means for rendering the first reagent non-covalently polymerizable. The second reagent contains means for rendering the second reagent detectable. The reagents and the sample are combined in the assay medium under conditions for polymerizing the first reagent wherein the second reagent becomes bound to the polymerized first reagent only when the analyte is present in the sample. After the first reagent has been polymerized, a determination is made as to whether the second reagent has become bound to the polymerized first reagent. If the second reagent can be detected in the polymerized first reagent, the presence of the polynucleotide analyte of interest is indicated.

Before proceeding further with a description of the specific embodiments of the present invention, a number of terms will be defined.

Polynucleotide analyte—a compound or composition to be measured which is a polymeric nucleotide having about 20 to 100,000 or more nucleotides, usually about 100 to 200,000 nucleotides, more frequently 500 15,000 nucleotides. The polynucleotide analytes include DNA, and RNA, including t-RNA, M-RNA, mitochrondrial RNA, genes, chromosomes, plasmids, the genomes of biological material such as microorganisms, e.g., bacteria, viruses, molds, fungi, and fragments thereof, and the like. Numerous examples of such biological material are disclosed in U.S. Pat. No. 4,351,760, particularly at columns 9 to 16, the disclosure of which is incorporated herein by reference. For purposes of this invention the polynucleotide analyte will usually be at least partially denatured or single stranded or treated to render it denatured. Such treatments are well known in the art and include, for instance, heat or alkali treatment. For example, double stranded DNA can be heated at 90°–100° C. for a period of about 1 to 10 minutes to produce denatured material.

Polymer-forming oligonucleotide—a homopolymer or copolymer of nucleotide residues that is bound directly or indirectly to a recognition polynucleotide to form a polymerization probe. Generally, for purposes of this invention the nucleotide residues appear in a repeating sequence. Examples of such repeating oligonucleotide sequences are found in "The Chemistry of Nucleic Acids", D. O. Jordan, Butterworth and Company Limited, 1960, particularly in chapters 13 and 14. The oligonucleotides employed in the present invention may be naturally occuring or synthetic, usually synthetic. Normally, there should be at least eight nucleotide residues, preferably at least 20 nucleotide residues. The upper limit for the number of nucleotide residues is not critical. Normally there is generally not more than 1,000 nucleotide residues, usually not more than 200 nucleotide residues. Particularly preferred in the present invention are homopolymeric oligonucleotides having at least eight nucleotides or heteropolymeric nucleotides consisting of two noncomplementary nucleotides having at least eight nucleotides residues. For example one may use in the present invention $(A)_{2n}$, $(C)_{2n}$, $(AC)_n$, $(GT)_n$, $(T)_{2n}$, wherein A is adenosine, C is cytidine, G is guanosine, T is thymidine, and n is usually a number between 4 and 1,000, preferably between 4 and 100.

Polymerization probe—a compound capable of hybridizing with the polynucleotide analyte and capable of being non-covalently polymerized. The polymerization probe is capable of hybridizing with the analyte by virtue of having a polynucleotide sequence complementary to a region of the polynucleotide analyte such that the polymerization probe will become bound to such region of the polynucleotide analyte. The polymerization probe is also capable of being non-covalently polymerized, that is, the polymerization probe is capable of forming a polymer wherein the polymeric bonds are noncovalent. Such bonds are formed primarily by electrostatic interactions, hydrophobic interactions, hydrogen bonding, dipole dipole interactions, and van der Waals interactions. In general, the polymerization probe will have two parts. The first part will be a "recognition oligonucleotide" sequence which is complementary to a region of the polynucleotide analyte. Generally this recognition oligonucleotide will contain from about 8 to 10,000 nucleotides, usually from about 20 to 2,000 nucleotides.

The second part of the polymerization probe provides a means for the probe to be non-covalently polymerized. For this purpose, the polymerization probe conveniently may contain a polymer-forming oligonucleotide as defined above. Such polymer-forming oligonucleotides are commercially avalable or can be synthesized readily. Other means for rendering the polymerization probe polymerizable include, for example, organic residues, which are bound to the probe, having molecular weights of 125–1500, such as biotin where the polymerization agent would comprise avidin or antibody for biotin, or in general one or more ligands or receptors may be bound to the probe when the polymerization agent comprises the complementary receptor or ligand, respectively.

The recognition oligonucleotide can be obtained by biological synthesis or by chemical synthesis. For short probes (up to 20 nucleotides) chemical synthesis will frequently be more economical as compared to the biological synthesis. In addition to economy, chemical synthesis provides a convenient way of incorporating low molecular weight compounds during the synthesis step. Furthermore, chemical synthesis is very flexible in the choice of length and region of the polynucleotide analyte. The recognition oligonucleotide sequence can be synthesized by standard methods such as those used in commercial automated nucleic acid synthesizers. For longer probes standard replication methods employed in molecular biology can be used such as those employed in commercial kits for preparation of RNA (e.g. from Promega) and by the use of a M13 plasmid for single stranded DNA as described by J. Messing (1983) *Methods Enzymol*, 101, 20–78.

The major criteria for choosing a recognition oligonucleotide sequence for the polymerization probe are:

(1) The sequence should be reliable, that is, the region to be synthesized must have been sequenced accurately and should be specific for the polynucleotide analyte.

(2) The sequence should be of sufficient length to provide stable and specific binding. The minimum unique sequence will usually be about 15 nucleotides although shorter sequences may be used where the specificity resides in the detection probe. In general, synthetic polynucleotides will be about 8 to 300 nucleotides, more frequently 15 to 50 nucleotides in length. With biologically synthesized polynucleotides random fragments of unknown sequences may be used provided however that nucleic acids are single stranded and complementary to the polynucleotide analyte. Methods for attaching the means for polymerization include incorporation of ligand labeled nucleotides in the probe during synthesis, polymerization of a polynucleotide tail onto the recognition sequence by means of, for example, nucleic acid polymerase, ligation of a preformed polymer forming oligonucleotide to the recognition sequence with, e.g., DNA ligase, or attachment of ligands to the preformed probe.

Detection probe—The detection probe is capable of hybridizing with the polynucleotide analyte at a region other than that with which the polymerization probe hybridizes. Furthermore, the detection probe is capable of being detected. Thus, the detection probe generally consists of two parts. One part of the detection probe renders the probe capable of hybridizing with the polynucleotide analyte in a region other than that which binds to the polymerization probe. For this purpose one can conveniently use a "recognition oligonucleotide" having a sequence which recognizes a region of the polynucleotide analyte not recognized by the recognition oligonucleotide of the polymerization probe. Such recognition oligonucleotide sequences may be ascertained and prepared as described above for the recognition oligonucleotide which is part of the polymerization probe.

The detection probe also includes a portion that renders the probe capable of being detected. Generally, the detection probe includes a label capable of producing a detectable signal either alone or by interaction with other members of a signal producing system. The label can initially be a part of or bound to a recognition oligonucleotide to form the detection probe or the label can bind to the detection probe during or after the polymerization of the first reagent or polymerization probe. In this regard, an sbp member, such as a specific polynucleotide sequence or a hapten, can be bound to a recognition oligonucleotide for form the detection probe and the label can be bound to a complementary sbp member. Exemplary of such sbp members and their complementary sbp members are antigens and antibodies, haptens and antibodies, biotin and avidin, an oligonucleotide and complementary oligonucleotide, an operon and its repressor, DNA-RNA heteroduplex and antibodies thereto and the like. Delaying the binding of the label to the detection probe as described above offers an advantage when hybridization of the detection probe with the analyte is impeded by the presence of the label or the label is unstable or insoluble under the hybridization conditions.

The two regions of the polynucleotide analyte complementary to the recognition oligonucleotides of the polymerization and detection probes will normally be in reasonable proximity to one another to ensure that a substantial fraction of the analyte will have the two regions linked. For purposes of the invention, the two regions will usually be within 5,000 kilobases (Kb), frequently with 2,000 Kb, more frequently within 500 Kb, but may be separated by 10,000 Kb or higher, particularly when the assay is used to demonstrate linkage of two nucleic acid sequences.

Polymerization agent—an agent that can bring about the non-covalent polymerization of the polymerization probe or the first reagent. Generally, the polymerization agent acts in conjunction with the means for polymerization of the polymerization probe to cause non-covalent polymerization of the polymerization probe wherein the means includes polymer forming oligonucleotides and other sbp members. When a polymer forming oligonucleotide is used, the polymerization agent will usually be an oligonucleotide that has a sequence complementary to the sequence of the polymer-forming oligonucleotide and can bind at least two copies of the polymer-forming oligonucleotide. The binding or hybridization between the oligonucleotides results in the non-covalent polymerization of the polymerization probe. When other sbp members are incorporated into the polymerization probe, the polymerization agent will be a complementary sbp member having at least two binding sites. Of course, the polymerization should not significantly interfere with the binding between the polynucleotide analyte and either of the recognition oligonucleotides, nor should it interfere with binding of the label to the detection probe.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs, such as biotin-avidin, hormones-hormone receptors, nucleic acid duplexes, IgG-protein A, DNA-DNA, DNA-RNA, and the like, are not immunological pairs but are included within the scope of this invention.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Support—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass, ceramics, metals, and the like.

Binding of sbp members to the support may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

Label—A member of the signal producing system that is conjugated to or becomes bound to the detection probe. In general, any label that is detectable by virtue of its being aggregated or spacially proximate to another label can be used. The label can be isotopic or nonisotopic, usually non-isotopic, and can be a catalyst, dye, fluorescent molecule, chemiluminescer, coenzyme, enzyme, and the like, and is preferably a particle such as latex or carbon particle, metal sol, crystallite, liposome, cell, etc. which may or may not be further labeled with a dye, catalyst or other detectible group. The label is a member of a signal producing system and can generate a detectable signal either alone or together with other members of the signal producing system. The label can be bound directly to the recognition polynucleotide of the detection probe or can become bound to the recognition polynucleotide by being bound to an sbp member complementary to an sbp member that is bound to the recognition polynucleotide.

Signal Producing System—The signal producing system may have one or more components, at least one component being the label. The signal producing system generates a signal that relates to the presence or amount of polynucleotide analyte in a sample. The signal producing system includes all of the reagents required to produce a measurable signal. When the label is not conjugated to the detection probe, the label is normally bound to an sbp member complementary an sbp member that is part of the detection probe. Other components of the signal producing system may be included in a developer solution and can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of the degree of aggregation of particles or by use of electromagnetic radiation, desirably by visual examination. For the most part, the signal producing system will involve particles, such as fluorescent particles or other light absorbing particles, a chromophoric substrate and enzyme, where chromophoric substrates are enzymatically converted to dyes which absorb light in the ultraviolet or visible region, phosphors, fluorescers or chemiluminescers.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of polynucleotide analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

The signal producing system can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/ml, and composed of material that can be transparent, partially transparent, or opaque.

The organic particles will normally be comprised of polymers, either addition or condensation polymers, which are readily dispersible in the assay medium. The surface of particles will be adsorptive or functionalizable so as to bind, either directly or indirectly, the oligonucleotide or an sbp member.

The particles can be derived from naturally occurring materials, naturally occurring materials which are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl funcationalities, and the like. Inorganic polymers include silicones, glasses, available as Bioglas, and the like. Natural or synthetic assemblies such as liposomes, phospholipid vesicles, and cells can also be employed.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of binding an oligonucleotide or an sbp member through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the particle on the hybridization of the probes and the polynucleotide analyte and the like. The oligonucleotide or sbp member will be substantially bound to the outer surface of the particle.

The particles can be fluorescent either directly or by virtue of fluorescent compounds or fluorescers bound to the particle in conventional ways. The fluorescers will usually be dissolved in or bound covalently or non-covalently to the particle and will frequently be substantially uniformly bound through the particle. Fluoresceinated latex particles are taught in U.S. Pat. No. 3,853,987 and are available commercially as Covaspheres from Covalent Technology Corp.

The fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes imines, anthracenes, oxacarboxyanine, merocyanine, 3-aminoequilenin, perylene, bis-benzoxazole, bis-p-oxazolyl benzene, 1,2-benzophenazine, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference.

Additionally, energy absorbent or quenching particles can be employed which are solid insoluble particles of at least about 50 nm in diameter capable of quenching the fluorescence of the fluorescent particle when within the distance resulting from hybridization of a prove with the polynucleotide analyte or from specific binding between members of specific binding pairs. The quenching particle may be the same or different, usually different, from the fluorescent particle. Normally, the quenching particle will provide a substantial quenching at a distance of more than about 50 A°, preferably more than about 500 A°, more preferably more than about 2000 A°, where the distance is measured from the surfaces of the particles.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver or copper sulfides or metal oxides, such as iron or copper oxide.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxy-substituents. Chemiluminescence may also be obtained with oxalates, usually oxalyl, active esters, e.g., p-nitrophenyl and a peroxide, e.g., hydrogen peroxide, under basic conditions. Alternatively, luciferins may be used in conjunction with luciferase or lucigenins.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, or surfactants, particularly non-ionic surfactants, binding enhancers, e.g., polyalkylene glycols, or the like.

As mentioned above the method of the present invention allows the determination of the presence of a polynucleotide analyte in a sample suspected of containing the analyte. The sample and first and second polynucleotide reagents complementary to the analyte are combined with an assay medium. Each of the first and second reagents hybridize with a different region of the analyte. The first reagent contains means for rendering the first reagent non-covalently polymerizable. Such first reagent can be, for example, a polymerization probe as described above. The second reagent contains means for rendering the second reagent detectable. The second reagent can be a detection probe as described above. The sample and the first and second reagents are combined in an assay medium under conditions for polymerizing the first reagent. Such conditions can be, for example, the introduction into the assay medium of a polymerization agent, e.g., an oligonucleotide having a sequence complementary to that of the polymer-forming oligonucleotide which forms part of the polymerization probe. The second reagent becomes bound to the polymerized first reagent only when the analyte is present in the sample. The first reagent is polymerized and a determination is made as to whether the second reagent has become bound to the polymerized first reagent. This can be accomplished by examining the medium or the polymer for the presence of a signal. For example, binding of the detection probe to the polymerized first reagent may be detected by examining the assay medium for the presence of aggregated particles, or examining either the polymerized first reagent or the assay medium for the presence of electromagnetic radiation.

In carrying out the method an aqueous medium will be employed. Other polar cosolvents may also be employed, usually oxygenated organic solvents of from 1–6, more usually from 1–4, carbon atoms, including alcohols, ethers and the like. Usually these cosolvents will be present in less than about 70 weight percent, more usually in less than about 30 weight percent.

The pH for the medium will usually be in the range of about 4–11, more usually in the range of about 5–10, and preferably in the range of about 6.4–9.5. The pH is chosen so as to maintain a significant level of hybridization, for binding to the polynucleotide analyte and for polymerizing the first reagent while optimizing signal producing proficiency. In some instances, a compromise will be made between these considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the method and usually constant temperatures during the period for conducting the method. The temperatures for the determination will generally range from about 0°–60° C., more usually from about 15°–45° C. As mentioned above, where the polynucleotide analyte is not single stranded, the sample must be treated to yield single stranded material. This can be accomplished conveniently, for example, by heating the sample to 90°-100° C. for 2 to 10 minutes either prior to or after addition of the polymerization and detection probes.

The concentration of polynucleotide analyte which cab be assayed will generally vary from about $10^{-15}$ to $10^{-6}$ g/ml, more usually from about $10^{-13}$ to $10^{-8}$ g/ml. Considerations such as whether the assay is qualitative, semi-quantitative or quantitative, the particular detection technique, and the concentration of the polynucleotide analyte will normally determine the concentration of the other reagents.

While the concentrations of the various reagents will generally be determined by the concentration range of interest of the polynucleotide analyte, the final concentration of each of the reagents will normally be determined empirically to optimize the sensitivity of the assay over the range of interest.

The concentration of the first and second reagents in the assay medium can vary widely; preferably, these reagents are present in an excess amount. The reagents will usually be present at least in an amount equivalent to the maximum suspected amount of polynucleotide analyte in the sample and may be present in 1.0 to $10^6$ fold or more excess, preferably at least $10^2$ fold excess.

The concentration of the polymerization agent in the assay medium can also vary substantially. The polymerization agent generally will be present in the assay medium in a molar concentration of below or equal to the polymerization probe concentration, preferably 0.1 to 0.8 times the polymerization probe concentration, more preferably 0.4 to 0.6 times the polymerization probe concentration.

The order of addition of the various reagents may vary. The second reagent can be combined with the assay medium and the sample prior to contacting the medium with the first reagent. The solution is then contacted with the polymerizing agent. However, simultaneous addition of the sample and the first and second reagents and the polymerizing agent, as well as other orders of addition, may be employed.

The concentration and order of addition of reagents and conditions for the assay are governed generally by the desire to maximize polymerization of the first reagent or polymerization probe.

As mentioned above the present assay method has particular application to homogeneous assays. Homogeneous assays are exemplified by immunofluorescence methods such as those disclosed in U.S. Pat. No. 3,993,345, enzyme channeling techniques such as those disclosed in U.S. Pat. No. 4,233,402, and other enzyme immunoassays as discussed in "Enzyme Immunoassay" by Edward T. Maggio, CRC Press Inc., Boca Raton, Fla. 1980 and in U.S. Pat. No. 3,817,837.

As mentioned above, an appropriate label and signal producing system are chosen to enable one to determine the extent that the detection probe becomes part of the polymerized polymerization probe in relation to the presence or amount of analyte in the sample. The following are some representative examples provided by way of illustration and not limitation.

In one approach the polymerization probe comprises a recognition oligonucleotide and a homopolymeric oligonucleotide, such as polyguanosine, of 8 to 20 nucleotides. The detection probe comprises a recognition oligonucleotide and an organic residue of molecular weight of about 125-1500, such as biotin. A receptor for the organic residue, such as avidin or antibody for biotin, is conjugated to particles that are part of a signal producing system. The particles are added to the assay medium. The polymerizing agent is a homopolymeric oligonucleotide complementary to that in the polymerization probe, such as polycytidylic acid in the case of polyguanosine. The particles become bound to the polymer only if both probes bind to the polynucleotide analyte. The particles can be fluorescent, for example, and after the method of the invention is carried out, any change in fluroescence can be measured by conventional means such as spectrophotometry or cytometry.

A non-flow cytometric technique can be used in the above measurement. A small diameter beam of light produced by means of slits or preferably a laser is used to differentiate particles based on their relative size by means of light scattering. This technique can also employ fluorescent pulse height analysis or correlation of fluorescence fluctuations: Briggs, et al., "Homogeneous Fluorescent Immunoassay," *Science,* 212, 1266-1267 (1981) and Nicoli, et al., "Fluorescence Immunoassay Based on Long Time Correlations of Number Fluctuations," *Proc. Natl. Acad. Asci. USA,* 77(8), 4904-4908 (1980).

A preferred method for determining a change of fluorescence in accordance with the present invention involves the use of a fiber optic cytometer described in U.S. patent application Ser. No. 397,285 filed July 12, 1982, the disclosure of which is incorporated herein by reference in its entirety. In that application, method and apparatus are provided for determining the presence of particles in a dispersion in relation to the detection of the presence or amount of a material of interest. An optical fiber is used to define a relatively small volume form which fluorescent light can be received and counted. The volume is related to the volume in which there is likely to be only a single particle which results in a predetermined fluctuation. By employing a variety of techniques, which allow for changes in fluorescence fluctuations in relation to the presence of an analyte in a sample, the amount of analyte present may be determined. The fluctuations are observed over a period of time in a static mode or by sampling a plurality of volumes in the sample. By comparing the observed results with results obtained with assay solutions having a known amount of analyte, the amount of analyte can be quantitatively determined.

In another approach in accordance with the present invention, the polymerization probe comprises a recognition oligonucleotide and a homopolymeric oligonucleotide, such as polyguanosine, of 8-20 residues. Two detection probes are used, one comprising a recognition oligonucleotide to which is bound a fluorescent compound as a label and the other a recognition oligonucleotide to which is bound a particle. The polymerization agent comprises a homopolymeric oligonucleotide complementary to that in the polymerization probe, such as polycytidylic acid in the case of polyguanosine. The method of the invention is carried out and the reaction medium is examined for fluorescence. By comparing the fluorescence of the particles with the fluorescence obtained with assay solutions having a known amount of analyte, the amount of analyte can be determined quantitatively.

In a variant of the above approach the detection probe can comprise an organic residue of molecluar weight of about 125-1500, such as biotin, bound to the detection oligonucleotide. Receptors for the organic residue, such as avidin or antibody for biotin in the case of biotin can be bound to the fluorescer and to the particles. This latter reagent can be added to the assay medium along with other members of the signal producing system and the results obtained as described above.

In another approach in accordance with the present invention, the polymerization probe comprises a recognition oligonucleotide and a homopolymeric oligonucleotide, such as polyguanosine, of 8-20 residues. The detection probe comprises a detection oligonucleotide to which is bound a first enzyme, such as horse radish peroxidase, as a label. The polymerization agent comprises a homopolymeric oligonucleotide complementary to that in the polymerization probe, such as polycytidylic acid in the case of polyguanosine, to which a second enzyme, such as glucose oxidase in the case of horse radish peroxidase, is bound. The enzymes are related in that the product of one is the substrate for the other. The method of the invention is carried out wherein the reaction medium includes all additional substrates and the like required for the enzyme signal producing system. The medium is examined for enzyme activity. By comparing the observed results with the results obtained with assay solutions having a known amount of analyte, the amount of analyte can be determined quantitatively.

In a variant of the above approach the detection probe can comprise an organic residue of molecular weight of about 125-1500, such as biotin, bound to the detection oligonucleotide. The first enzyme can be bound to a receptor for the organic residue, such as avidin or antibody for biotin in the case of biotin. This latter reagent can be added to the assay medium along with the members of the signal producing system and results obtained as described above.

In the above approaches, one of the reagents can also be attached to a support.

As a matter of convenience, the reagents employed in the present invention can be provided in a kit in packaged combination with predetermined amounts of reagents for use in assaying for a polynucleotide analyte in a sample. For example, a kit useful in a method for determining the presence of a polynucleotide analyte in a sample suspected of containing said analyte can comprise in packaged combination: (a) a polymerization probe comprising (1) a polynucleotide, complementary with a region of said analyte, conjugated to (2) means for rendering said polymerization probe non-covalently polymerizable, (b) a detection probe comprising (1) a polynucleotide, complementary with a region of said analyte other than the region recognized by said polymerization probe, conjugated to (2) means for rendering said polymeric detection probe detectable, (c) a polymerization agent capable of causing the non-covalent polymerization of said polymerization probe, and (d) ancillary materials as required.

Where particles are employed as the label, the kit can further comprise any reagents necessary to incorporate the particles into the polymerized polymerization probe. For example, such reagent can be a receptor for an organic residue bound to the detection probe, which receptor is conjugated to the particles.

Where an enzyme is used as the label, the reagents can include an enzyme labeled sbp member, substrate for the enzyme, or precursors therefor, including any additional substrates, enzymes and cofactors and any reaction partner of the enzymic product required to provide a detectable chromophore or fluorophore, and any other members of a signal producing system.

The relative amounts of the various reagents in the kits can be varied widely to provide for concentrations in solution of the reagents which substantially optimize the sensitivity of the assay. In addition, the reagents in the kit can be provided as dry powders, usually lyophilized, including excipients, which on dissolution will provide for a reagent solution having the appropriate concentrations for performing the assay.

EXAMPLES

The invention is demonstrated further by the following illustrative examples. Temperatures are in degrees centigrade (°C.). Parts and percentages are by weight unless otherwise specified.

The following abbreviations were used in the description of the examples.

dUTP—deoxyuridine triphosphate
dGTP—deoxyguanosine triphosphate
HPLC—high performance liquid chlomotography
$\alpha^{32}$PATP—$\alpha^{32}$P adenosine triphosphate
HSV TK—herpes virus thymidine kinase
DTT—dithiothrietol
EDTA—ethylenediaminetetraacetate
EDAC—1-ethyl-3-(3-dimethylaminopropyl)carbodiimide
SDS—sodium dodecyl sulfate
TE—10 mM Tris·Cl, 1 mM EDTA
L-Broth—LB(Luria-Bertani) Medium
ds—double stranded
Squarate dye—1,1'-(4,4'-bisdihexadecylaaminophenyl)carbo-1,3-squairane prepared by a procedure similar to that described by Springer, et al., *Angew. Chem.*, 80, 541 (1968).
BSA—bovine serum albumin The nucleoside triphosphates with the exception of biotin dUTP were purchased from P. L. Biochemicals. Biotin dUTP was purchased from Enzobiochem. Radioactive nucleotides were purchased from New England Nuclear. Polynucleotide Kinase, DNA polymerase I, terminal transferase (Minimal Nuclease) and restriction endonucleases were obtained from either P. L. Biochemicals or Bethesda Research Laboratories. Most of the protocols for use of these enzymes were taken from suppliers technical literature.

EXAMPLE 1

Preparation of Avidin Coated Latex Beads

EDAC (37.5 mg) was added portion wise to a suspension of stock squarate dye labeled latex beads (0.82 ml, 0.71 μm, $4.5 \times 10^{11}$ beads/ml) and diluted to a volume of 4 mls. Avidin D (Vector Laboratories) (2 mgs) in 0.1N NaCl (2 ml) was next added. The mixture was sonicated and mixed overnight at room temperature. After workup by centrifugation and washing with GBS buffer (0.17N glycine, 0.1N NaCl, 7.6 mM NaN$_3$, pH 9.2)—1% BSA, the beads were suspended in 6 mls of GBS buffer—1% BSA to give a stock solutin of $6 \times 10^{10}$ beads/ml.

EXAMPLE 2

Synthesis of Oligonucleotide Probes

Oligonucleotide 5'CGTGTTTGCCTGGGCCTTGG3' (Probe A) and 5'GCCCCAGAGCAACGAC3' (Probe B) were synthesized according to published procedures for synthesizing other oligonucleotides on silica gel solid support and phosphite triester chemistry and nucleoside phosphamidites as the building blocks. The basic chemistry and the repeating cycles are described by Sinha, et al. in *Nucleosides and Nucleotides*, 3(2), 157–171 (1984). The probes after deblocking were purified by HPLC on a CIP sperisorb column. The oligonucleotides were characterized by labeling with $^{32}P$ using $\alpha^{32}PATP$ and polynucleotide kinase and hybridizing to dot blots of HSV TK gene DNA.

EXAMPLE 3

Conjugation of Probe B and Biotin

To a mixture of 300 p mole of oligonucleotide, prepared as described in Example 2, 3 n mole of biotinylated dUTP in 130 μl terminal transferase buffer (140 mM cacodylate, 30 mM tris base, 1 mM DTT and 1 mM $CoCl_2$) was added 200 units deoxynucleotidyl terminal transferase. The mixture was incubated at 37° for 2 hours. The mixture was then passed through a G-50 Sephadex column to give biotinylated Probe B product. The column was calibrated by passing a mixture of $^{32}P$ labeled oligonucleotide and $^{32}P$ triphosphate through the column.

EXAMPLE 4

Preparation of G Tailed Probe A

To a solution of 100 p moles of oligonucleotide Probe A prepared as described in Example 2 and 10 n moles of dGTP in 100 μl of Terminal transferase buffer (140 mM cacodylate, 30 mM tris base, 1 mM DTT and 1 mM $CoCl_2$) were added 200 units of terminal transferase. The mixture was incubated at 37° for 2 hours, followed by heating at 70° for 2 minutes to inactivate the enzyme. The tailed oligonucleotide probe A was purified by passing through a G-50 sephadex column to give the G tailed Probe A product.

EXAMPLE 5

Preparation of pHSV 106 DNA pHSV 106 DNA is a pBR322 derivative containing Herpes simplex virus I, thymidine kinase gene sequences inserted into the Bam HI site. The *E.coli* strain containing the pHSV 106 plasmid was obtained by conventional molecular cloning techniques. The procedure for preparing the DNA was adapted from Cold Spring Harbor Molecular Cloning Laboratory Manual.

500 ml of L Broth were innoculated with 5 ml of an overnight growth culture of the pHSV106 *E. coli* strain. The cells were grown overnight and were pelleted by centrifugation for 10 minutes at 4° C. The pellet was suspended in 10 ml of a pH 7.5 solution containing 50 mM glucose, 25 mM Tris HCl, 10 mM EDTA and 5 mg/ml lysozyme. The contents were transferred to a Beckman SW27 polyallomer tube and allowed to stand at room temperature for 5 minutes. To this mixture 20 ml of solution containing 0.2N NaOH and 20% SDS were added. The contents, after covering with parafilm, were mixed by gently inserting the tube several times and then allowed the tubes to stand in ice for 10 minutes. An ice cold solution of 5M potassium acetate (pH4.5) (15 ml) was added and the contents left in ice for 10 minutes. The tube was then centrifuged on a Beckman SW27 rotor at 20,000 rpm for 20 minutes at 4° C. The cellular DNA and the bacterial debris formed a tight pellet on the bottom of the tube. The clear supernatant was transferred to two 20 ml tubes (made from Corex® material), 0.6 volumes of isopropanol were added to each tube, and the contents after thorough mixing were kept at room temperature for 15 minutes. The DNA was recovered by centrifugation in a Sorval centrifuge at 12,000 g for 30 minutes. The pellet was washed with 70% ethanol and dried in a vacuum desicator. The pellet was then dissolved in 8 ml TE buffer (pH 8.0) and 8 g of CsCl added. The DNA was banded at 45,000 RPM for 24 hours after adding ethidium bromide. The lower band was collected and extracted with isopropanol saturated with water. After removal of ethidium bromide the solution was extensively dialyzed against TE.

EXAMPLE 6

Digestion of pHSV 106 DNA with Restriction Endonuclease Bam HI

The purified DNA prepared as described in Example 5 was linearized by digestion with Bam HI. A typical digestion involved 10 μg of DNA in 100 μl of buffer containing 10 mM tris pH 7.5, 50 mM NaCl, 10 mM $MgCl_2$ and 1 mM dithiothreitol; 20 units of enzyme were added and the incubation carried out at 37° for 1 hour. The reaction was terminated by heating the sample at 65° for 3 minutes and the product was used directly.

EXAMPLE 7

Assay

A solution of 250 ng of dsDNA containing 30 f moles DNA from Example 5 and ~1 p mole of G-tailed Probe A in 20 μl water in a capped Eppendorf tube were heated in a boiling water bath for 3 minutes. The tube was quickly transferred to a wet ice bath and immediately 1 p mole of biotinylated probe B in 2 μl solution containing 1M Tris HCl pH 8.0 and 2.5M NaCl were added. The contents were left in the ice bath for 10 minutes for the hybridization to occur and hybrid DNA was recovered.

To the solution containing the hybrid DNA was added a sonicated suspension of ~$10^9$ beads containing covalently bound avidin prepared as described in Example 1 and included squarate dye in 10 μl of buffer containing 50 mM TRIS pH 9.0, 15M NaCl, 5% ovalbumin 0.05% Tween and 10 mM EDTA. The contents were shaken on a platform shaker for 10 minutes. After this period 2 μl of a 10 ng/ml solution of polycytidylic acid (poly C) were added and the contents stirred for another 10 minutes. This suspension (2 μl) was diluted 250 fold and the average diameter of the beads was measured by taking the mean diameter of the beads in each case. Greater than 50,000 measurements were made for each experiment using a Nicomp laser spectrophotometer. The results are summarized in Table 1.

TABLE 1

| Experiment | | Size $10^3$ nm |
|---|---|---|
| $1^a$ | Test DNA + Biotinylated Probe B + G-tailed Probe A + Poly C + Avidin coated Beads | 2.4 |
| $2^b$ | Avidin coated beads | 1.02 |
| $3^b$ | Test DNA + Biotinylated probe B + G-tailed Probe A + Poly C + biotin + Avidin coated beads | 1.18 |
| $4^b$ | Test DNA + G-tailed Probe A + Poly C + Avidin coated beads | 1.32 |
| $5^b$ | Test DNA + Biotinylated Probe B + Poly C + | 1.84 |

TABLE 1-continued

| Experiment | Size $10^3$ nm |
|---|---|
| Avidin coated beads | |

[a]in accordance with the present invention
[b]not in accordance with the present invention but provided for purposes of comparison.

The above results indicate that a rapid, accurate, sensitive assay for polynucleotide analytes can be carried out in accordance with the invention described herein. The assay is readily automatable. In Experiment 1 conducted in accordance with the present invention, a significantly larger average particle diameter was observed over that observed in Experiments 2-5. Consequently, the improvement of using complementary oligonucleotide sequences to cause agglutination in an assay for a polynucleotide analyte is demonstrated. In the agglutination two probes are employed and both are required to hybridize to the polynucleotide analyte.

The invention has been described in detail with particular reference to the above embodiments. It will be understood, however, that variations and modifications can be effected within the spirit and scope of the invention.

What is claimed is:

1. A method for determining the presence of a polynucleotide analyte in a sample suspected of containing said analyte, which method comprises
   (a) combining in an assay medium said sample and first and second polynucleotide reagents complementary to said analyte, wherein each of said first and second reagents hybridizes with a different region of said analyte, said first reagent containing means for rendering said first reagent non-covalently polymerizable and said second reagent containing means for rendering said second reagent detectable, wherein, under conditions for polymerizing said first reagent, said second reagent becomes bound to said polymerized first reagent only when said analyte is present in said sample,
   (b) non-covalently polymerizing said first reagent, and
   (c) determining whether said second reagent has become bound to said polymerized first reagent.

2. The method of claim 1 wherein a compound capable of causing the non-covalent polymerization of said first reagent is combined in Step b.

3. The method of claim 1 wherein said polynucleotide analyte is DNA.

4. The method of claim 1 wherein said polynucleotide analyte is RNA.

5. The method of claim 1 wherein Step c said polymerized first reagent is examined for the presence of said second reagent by determining the presence of aggregated particles.

6. The method of claim 1 wherein said polynucleotide analyte is selected from the group consisting of genomes of viruses, bacteria, and fungi, and fragments thereof.

7. The method of claim 6 wherein the fungi are molds.

8. The method of claim 1 wherein said means for rendering said first reagent non-covalently polymerizable includes a first specific binding pair (sbp) member bound to said first reagent and wherein a second sbp member complementary to said first sbp member having at least two specific binding sites for said sbp member is combined with said assay medium.

9. The method of claim 8 wherein said sbp member and said complementary sbp member are selected from the group consisting of antigen-antibody, avidin-biotin, IgG-protein A, DNA-DNA and DNA-RNA.

10. The method of claim 1 wherein said means for rendering said first reagent non-covalently polymerizable includes a repeating oligonucleotide sequence covalently bound to said first reagent.

11. The method of claim 10 wherein said repeating oligonucleotide sequence is a homopolymer having at least 8 nucleotide residues.

12. The method of claim 10 wherein said repeating oligonucleotide sequence is a heteropolymer at least eight nucleotides in length consisting of two non-complementary nucleotides.

13. The method of claim 1 wherein said means for rendering said second reagent detectable includes a first specific binding pair (sbp) member bound to said second reagent and a second sbp member complementary to said first sbp member bound to said label wherein at least one of said first or second sbp members has only one specific binding site.

14. The method of claim 13 wherein said sbp member is an organic residue of molecular weight 125-1500 covalently bound to said second reagent and said complementary sbp member is a receptor specific for said organic residue.

15. The method of claim 13 wherein said label is selected from the group consisting of catalysts, fluorescers, chemiluminescers, and particles.

16. The method of claim 13 wherein said sbp member and said complementary sbp member are respectively a ligand of molecular weight 125-1500 and a receptor for said ligand, wherein a single ligand is bound to said second reagent.

17. The method of claim 16 wherein said ligand is biotin and said receptor is avidin.

18. The method of claim 1 wherein said means for rendering said second reagent detectable includes a label selected from the group consisting of catalysts, dyes, fluorescers, chemiluminescers, and particles.

19. The method of claim 18 wherein said label is selected from the group consisting of metal sols, carbon particles, polymeric particles, liposomes, and dye aggregates.

20. The method of claim 18 wherein said label is a fluorescent particle.

21. The method of claim 18 wherein a second label is employed.

22. The method of claim 21 wherein said label is a first enzyme and said second label is a second enzyme wherein said enzymes are related in that the product of one is the substrate for the other.

23. The method of claim 21 wherein said label is a fluorescer and said second label is a quencher.

24. The method of claim 21 wherein said second label is covalently or noncovalently bound to a compound capable of causing the non-covalent polymerization of said first reagent.

25. A method for determining the presence of a polynucleotide analyte in a sample suspected of containing said analyte, which method comprises
   (a) combining in an assay medium said sample,
      (A) a polymerization probe capable of hybridizing with said analyte and capable of being non-covalently polymerized, and (B) a detection probe capable of hybridizing with said analyte in a region other than that with which said non-covalent polymerization probe hybridizes and capable of being detected, which detection probe becomes bound to the polymerized polymerization probe only when said analyte is present in said sample, (b) causing the polymerization of said polymerization probe, and (c) determining whether said detection probe is bound to said polymerized polymerization probe.

26. The method of claim 25 wherein a compound capable of causing the non-covalent polymerization of said polymerization probe is combined in Step b.

27. The method of claim 25 wherein said polynucleotide analyte is DNA.

28. The method of claim 25 wherein said polynucleotide analyte is RNA.

29. The method of claim 25 wherein in Step c said polymerized polymerization probe is examined for the presence of said detection probe by determining the presence of aggregated particles.

30. The method of claim 25 wherein said polynucleotide analyte is selected from the group consisting of genomes of viruses, bacteria, and fungi and fragments thereof.

31. The method of claim 30 wherein the fungi are molds.

32. The method of claim 25 wherein said polymerization probe comprises an oligonucleotide, complementary to a portion of said analyte, bound to means for rendering said polymerization probe non-covalently polymerizable.

33. The method of claim 32 wherein said means includes a repeating oligonucleotide sequence covalently bound to said polymerization probe.

34. The method of claim 32 wherein said oligonucleotide is a homopolymer having at least eight nucleotide residues.

35. The method of claim 32 wherein said oligonucleotide is a heteropolymer containing at least eight nucleotides comprising two non-complementary nucleotides.

36. The method of claim 32 wherein said means includes a specific binding pair (sbp) member bound to said polymerization probe and wherein a complementary sbp member having at least two specific binding sites is combined with said assay medium.

37. The method of claim 36 wherein said sbp member and said complementary sbp member are selected from the group consisting of antigen-antibody, avidin-biotin, IgG-protein A, DNA-DNA and DNA-RNA.

38. The method of claim 25 wherein said detection probe comprises an oligonucleotide bound to a means for rendering said detection probe detectable.

39. The method of claim 38 wherein said means includes a label selected from the group consisting of catalysts, dyes, fluorescers, chemiluminescers, particles, metal sols, carbon particles, polymeric particles, liposomes, and dye aggregates.

40. The method of claim 39 wherein said label is a fluorescent particle.

41. The method of claim 39 wherein said label is selected from the group consisting of catalysts, dyes, enzymes, coenzymes, fluorescers, quenchers, chemiluminescers, particles, metal sols, carbon particles, polymeric particles, lyposomes, and dye aggregates.

42. The method of claim 39 wherein a second label is employed.

43. The method of claim 42 wherein said label is a first enzyme and said second label is a second enzyme wherein said enzymes are related in that the product of one is the substrate for the other.

44. The method of claim 42 wherein said label is a fluorescer and said second label is a qunecher.

45. The method of claim 42 wherein said second label is bound to, or is capable of binding to, a compound capable of causing the non-covalent polymerization of said polymerization probe.

46. The method of claim 39 wherein said means includes a first specific binding pair (sbp) member bound to said detection probe and a second sbp member complementary to said first sbp member bound to said label wherein at least one of said first or second sbp members has a single specific binding site.

47. The member of claim 46 wherein said sbp member is an organic residue of molecular weight 125-1500 covalently bound to said detection probe and said complementary sbp member is specific for said organic residue.

48. The method of claim 46 wherein said sbp member and said complementary sbp member are respectively a ligand of molecular weight 125-1500 and a receptor wherein a single ligand is bound to said detection probe.

49. The method of claim 48 wherein said ligand is biotin and said receptor is avidin.

50. A method for determining the presence of a polynucleotide analyte in a sample suspected of containing said analyte, which method comprises (a) combining in an assay medium said sample and (A) a polymerization probe comprising (1) a polynucleotide, hybridizable with a region of said analyte, conjugated to (2) means for non-covalently polymerizing said polymerization probe, (B) a detection probe comprising (1) a polynucleotide, hybridizable with a region of said analyte other than the region recognized by said polymerization probe, conjugated to (2) means for rendering said detection probe detectable, and (C) a polymerization agent capable of causing the non-covalent polymerization of said polymerization probe, under conditions for polymerizing said polymerization probe wherein said detection probe becomes bound to said polymerized polymerization probe only when said analyte is present in said sample, and (b) determining whether said detection probe has become bound to said polymerized polymerization probe.

51. The method of claim 50 wherein said polynucleotide analyte is DNA.

52. The method of claim 50 wherein said polynucleotide analyte is RNA.

53. The method of claim 50 wherein in Step b said polymerized polymerization probe is examined for the presence of said detection probe by determining the presence of aggregated particles.

54. The method of claim 50 wherein said polynucleotide analyte is selected from the group consisting of genomes of viruses, bacteria, and fungi, and fragments thereof.

55. The method of claim 54 wherein the fungi are molds.

56. The method of claim 50 wherein said means for non-covalently polymerizing said polymerization probe includes a repeating oligonucleotide sequence covalently bound thereto.

57. The method of claim 56 wherein said repeating oligonucleotide sequence is a heteropolymer containing at least eight nucleotides and comprising two non-complementary nucleotides.

58. The method of claim 50 wherein said means for rendering said polymeric detection probe detectable includes a label selected from the group consisting of catalysts, dyes, fluorescers, quenchers, chemiluminescers, particles, metal sols, carbon particles, polymeric particles, liposomes, and dye aggregates.

59. The method of claim 58 wherein said label is a fluorescent particle.

60. The method of claim 58 wherein a second label is employed.

61. The method of claim 60 wherein said label is a first enzyme and said second label is a second enzyme wherein said enzymes are related in that the product of one is the substrate for the other.

62. The method of claim 60 wherein said label is a fluorescer and said second label is a quencher.

63. The method of claim 60 wherein said second label is bound to, or may become bound to, a polymerization agent capable of causing the non-covalent polymerization of said polymerization probe.

64. The method of claim 58 wherein said means for rendering said polymeric detection probe detectable includes a first specific binding pair (sbp) member bound to said detection probe and a second sbp member complementary to said first sbp member bound to said label wherein at least one of said first or second sbp members has a single specific binding site.

65. The method of claim 64 wherein said sbp member and said complementary sbp member are selected from the group consisting of antigen-antibody, avidin-biotin, IgG-protein A, DNA-DNA, and DNA-RNA.

66. The method of claim 64 wherein said label is selected from the group consisting of catalysts, dyes, fluorescers, chemiluminescers, particles, metal sols, carbon particles, polymeric particles, liposomes, and dye aggregates.

67. A method for determining the presence of a polynucleotide analyte in a sample suspected of containing said analyte, which method comprises
(a) combining in an assay medium said sample and
(A) a polymerization probe comprising (1) a polynucleotide, hybridizable with a region of said analyte, bound to (2) a repeating oligonucleotide sequence selected from the group consisting of a homopolymer having at least eight nucleotide residues and a heteropolymer consisting of two non-complementary nucleotides in a nucleotide sequence at least eight nucleotides in length,
(B) a detection probe comprising (1) a polynucleotide, hybridizable with a region of said analyte other than the region recognized by said polymerization probe, bound to (2) a label selected from the group consisting of catalysts, enzymes, coenzymes, dyes, fluorescers, chemiluminescers, and particles, and
(C) a polymerizing agent comprising a repeating oligonucleotide sequence complementary to said repeating oligonucleotide sequence bound to said polymerization probe,
(b) causing polymerization of said polymerization probe under conditions wherein said detection probe becomes bound to said polymerized polymerization probe only if said analyte is present in said sample, and
(c) determining whether said detection probe has become bound to said polymerized polymerization probe.

68. The method of claim 67 wherein said polymerized polymerization probe is examined for the presence of said detection probe by determining the presence of aggregated particles.

69. The method of claim 67 wherein a second label is employed.

70. The method of claim 69 wherein said label is a first enzyme and said second label is a second enzyme wherein said enzymes are related in that the product of one is the substrate for the other.

71. The method of claim 69 wherein said label is a fluorescer and said second label is a quencher.

72. The method of claim 69 wherein said second label is conjugated to, or may become conjugated to, said polymerization agent.

73. In an assay method for the detection of a polynucleotide analyte in a sample suspected of containing said analyte, said method comprising the steps of combining said sample with a reagent capable of hybridizing with said analyte and determining the extent of such hybridization, the improvement which comprises employing a nucleotide sequence to cause non-covalent polymerization to determine the extent of such hybridization.

74. The method of claim 73 wherein said polynucleotide analyte is DNA.

75. The method of claim 73 wherein said polynucleotide analyte is RNA.

76. The method of claim 73 wherein said polynucleotide analyte is the genome of herpes virus.

77. The method of claim 73 wherein said agglutination employs repeating oligonucleotide sequences having at least eight nucleotide residues.

78. The method of claim 73 wherein said nucleotide sequence is a heteropolymer at least eight nucleotides in length comprising two repeating non-complementary nucleotides.

79. The method of claim 73 wherein said polynucleotide analyte is selected from the group consisting of genomes of viruses, bacteria, and fungi, and fragments thereof.

80. The method of claim 79 wherein the fungi are molds.

81. A kit useful in a method for determining the presence of a polynucleotide analyte in a sample suspected of containing said analyte, which kit comprises in packaged combination
(a) polymerization probe comprising (1) a polynucleotide, complementary with a region of said analyte to an extent sufficient to hybridize to said analyte, conjugated to (2) means for rendering said polymerization probe non-covalently polymerizable,
(b) a detection probe comprising (1) a polynucleotide, complementary with a region of said analyte, to an extent sufficient to hybridize to said analyte, other than the region recognized by said polymerization probe, conjugated to (2) means for rendering said detection probe detectable, and
(c) a polymerization agent for causing the non-covalent polymerization of said polymerization probe.

82. The kit of claim 81 wherein the means for rendering said polymerization probe non-covalently polymerizable includes a repeating oligonucleotide sequence and said polymerization agent is a repeating oligonucleotide sequence complementary to said sequence.

83. The kit of claim 81 wherein said means for rendering said polymerization probe non-covalently polymerizable includes a specific binding pair (sbp) member bound thereto and wherein said kit further comprises a complementary sbp member having at least two specific binding sites.

84. The kit of claim 83 wherein said sbp member and said complementary sbp member are selected from the group consisting of antigen-antibody, avidin-biotin, IgG-protein A, DNA-DNA, and DNA-RNA.

85. The kit of claim 81 wherein said means for rendering said polymerization probe non-covalently polymerizable includes a repeating oligonucleotide sequence.

86. The kit of claim 85 wherein said repeating nucleotide sequence is a homopolymer having at least eight nucleotide residues.

87. The kit of claim 85 wherein said repeating nucleotide sequence is a heteropolymer having at least eight nucleotide residues comprising two non-complementary nucleotides.

88. The kit of claim 81 wherein said means for rendering said polymeric detection probe detectable includes a label selected from the group consisting of catalysts, enzymes, coenzymes, dyes, fluorescers, quenchers, chemiluminescers and particles.

89. The kit of claim 88 which further includes a second label conjugated to a compound capable of causing the non-covalent polymerization of said polymerization probe.

90. The kit of claim 89 wherein said label is a first enzyme and said second label is a second enzyme wherein said enzymes are related in that the product of one is the substrate for the other.

91. The kit of claim 89 wherein said label is a fluorescer and said second label is a quencher.

92. The kit of claim 88 wherein said means for rendering said detection probe detectable includes a first specific binding pair (sbp) member bound to said detection probe and said kit further comprises a second sbp member complementary to said first sbp member bound to said label wherein at least one of said first and second sbp members has a single specific binding site.

93. The kit of claim 92 wherein said sbp member is an organic residue of molecular weight 125–1500 covalently bound to said detection probe and said complementary sbp member is a receptor specific for said residue.

94. The kit of claim 92 wherein said label is selected from the group consisting of catalyts, enzymes, coenzymes, dyes, fluorescers, quenchers, chemiluminescers, and particles.

95. The kit of claim 92 wherein said sbp member and said complementary sbp members are respectively a ligand of molecular weight 125–1500 and a receptor wherein a single ligand is bound to the detection probe.

96. The kit of claim 95 wherein said organic residue is biotin and said receptor is avidin.

* * * * *